US008141440B2

(12) United States Patent
Gammon et al.

(10) Patent No.: US 8,141,440 B2
(45) Date of Patent: Mar. 27, 2012

(54) SYSTEM FOR COLLECTING A FLUID SAMPLE FROM A TRANSIENT LINE OF FLUID

(75) Inventors: Howard M. Gammon, Lakewood, NJ (US); James H. Gammon, Manasquan, NJ (US)

(73) Assignee: Gammon Technical Products, Inc., Manasquan, NJ (US)

( * ) Notice: Subject to any disclaimer, the term of this patent is extended or adjusted under 35 U.S.C. 154(b) by 228 days.

(21) Appl. No.: 11/718,155

(22) PCT Filed: Apr. 26, 2007

(86) PCT No.: PCT/US2007/067482

§ 371 (c)(1),
(2), (4) Date: Apr. 26, 2010

(87) PCT Pub. No.: WO2007/127832

PCT Pub. Date: Nov. 8, 2007

(65) Prior Publication Data

US 2010/0206097 A1    Aug. 19, 2010

Related U.S. Application Data

(60) Provisional application No. 60/795,447, filed on Apr. 27, 2006.

(51) Int. Cl.
*G01N 1/12* (2006.01)

(52) U.S. Cl. ............... 73/864.63; 73/863.71; 73/863.73
(58) Field of Classification Search ............... 73/863.71, 73/863.72, 863.73, 863.81, 863.86, 864.52, 73/864.63
See application file for complete search history.

(56) References Cited

U.S. PATENT DOCUMENTS

| 4,252,021 A | 2/1981 | Drushel |
| 5,251,495 A * | 10/1993 | Kuhner ............... 73/863.71 |
| 5,370,005 A | 12/1994 | Fjerdingstad |
| 6,289,752 B1 * | 9/2001 | Nimberger et al. ........ 73/863.11 |

FOREIGN PATENT DOCUMENTS

| WO | WO2004057306 A1 | 7/2004 |
| WO | WO 2008111851 A1 | 9/2008 |

* cited by examiner

*Primary Examiner* — Daniel Larkin
(74) *Attorney, Agent, or Firm* — Fraser Clemens Martin & Miller LLC; J. Douglas Miller

(57) ABSTRACT

A closed loop system for obtaining a sample of a fluid from a source of fluid is disclosed, the system including a collection vessel having a fluid chamber disposed therein. A valve assembly is disposed within the collection vessel and adapted to selectively open and close a fluid communication path between the fluid chamber and an associated fluid receptacle. An inlet provides a fluid communication path between the source of fluid and the fluid chamber, and an outlet provides a fluid communication path between the fluid chamber and a fluid recovery system.

20 Claims, 3 Drawing Sheets

SYSTEM FOR COLLECTING A FLUID SAMPLE FROM A TRANSIENT LINE OF FLUID

CROSS-REFERENCE TO RELATED APPLICATION

This application claims the benefit of U.S. Provisional Patent Application Ser. No. 60/795,447 filed on Apr. 27, 2006.

FIELD OF THE INVENTION

The invention relates to a system for collecting a fluid sample, and more particularly to a closed loop system for collecting a test sample of fluid from a transient line of fluid.

BACKGROUND OF THE INVENTION

It is necessary to periodically test aviation fuel to determine whether the fuel has been contaminated by the presence of free water.

Among the techniques employed to achieve the desired testing includes the filling of a container with a quantity of the fuel to be tested. A fixture having an extending hypodermic needle is disposed at the bottom of the container. A glass vial having a rubber stopper is urged against the needle causing the needle to extend through the rubber stopper. The interior of the glass vial is under vacuum causing the fuel to be tested to be drawn into the vial. A powdered chemical, previously inserted into the vial, is contacted by the incoming fuel. In the event the fuel contains more than the acceptable amount of water, typically 30 ppm, the chemical changes color.

The act of drawing a sample of fuel from the fueling system into an open container is messy and also allows the introduction of additional contamination such as water from rain, for example. Such a procedure introduces an undesirable source of an error in the test.

It would be desirable to produce a system for collecting a sample of aviation fuel to test for the presence of free water wherein the fuel to be tested can be caused to flow directly from an aircraft fuel handling system into an optically transparent vial containing a powdered chemical which changes color upon contact with free water.

SUMMARY OF THE INVENTION

Compatible and attuned with the present invention, a system for obtaining a sample of aviation fuel to test for the presence of free water wherein the fuel to be tested can be caused to flow directly from an aircraft fuel handling system into an optically transparent vial containing a powdered chemical which changes color upon contact with free water has surprisingly been discovered.

In one embodiment, a closed loop system for collecting a fluid sample from a source of fluid comprises a collection vessel including a fluid chamber disposed therein; a collection vessel including a fluid chamber disposed therein; a valve assembly adapted to selectively open and close a fluid communication path between the fluid chamber and an associated fluid receptacle; an inlet providing fluid communication between the source of fluid and the fluid chamber; and an outlet providing fluid communication between the fluid chamber and a fluid recovery system.

In another embodiment, a closed loop system for collecting a fluid sample from a source of fluid comprises a collection vessel including a fluid chamber disposed therein; a valve assembly adapted to selectively open and close a fluid communication path between the fluid chamber and an associated fluid receptacle, the valve assembly including an elongate shaft having one end and a spaced apart other end; a valve body having one end and a spaced apart other end, the one end including attachment means adapted to secure the other end of the elongate shaft thereto; and a spring having one end and a spaced apart other end, the spring surrounding at least a portion of the elongate shaft, the one end abutting an inner surface of the fluid chamber and the other end abutting the one end of the valve body, the spring urging the valve assembly to position wherein the fluid communication path is normally closed; an inlet providing fluid communication between the source of fluid and the fluid chamber; and an outlet providing fluid communication between the fluid chamber and a fluid recovery system.

In another embodiment, a method for collecting a fluid sample from a transient line of fluid comprises the steps of providing a collection vessel in fluid communication with the transient line of fluid; opening a valve to cause the fluid to flow from the transient line through the collection vessel; retaining a sample of the fluid in a fluid chamber within the collection vessel; and drawing the sample of fluid from the fluid chamber through a communication path into a fluid receptacle.

BRIEF DESCRIPTION OF THE DRAWINGS

The above, as well as other objects and advantages of the invention, will become readily apparent to those skilled in the art from reading the following description of an embodiment of the invention when considered in the light of the accompanying drawings, in which.

DETAILED DESCRIPTION OF THE PREFERRED EMBODIMENT OF THE INVENTION

Figure 1:
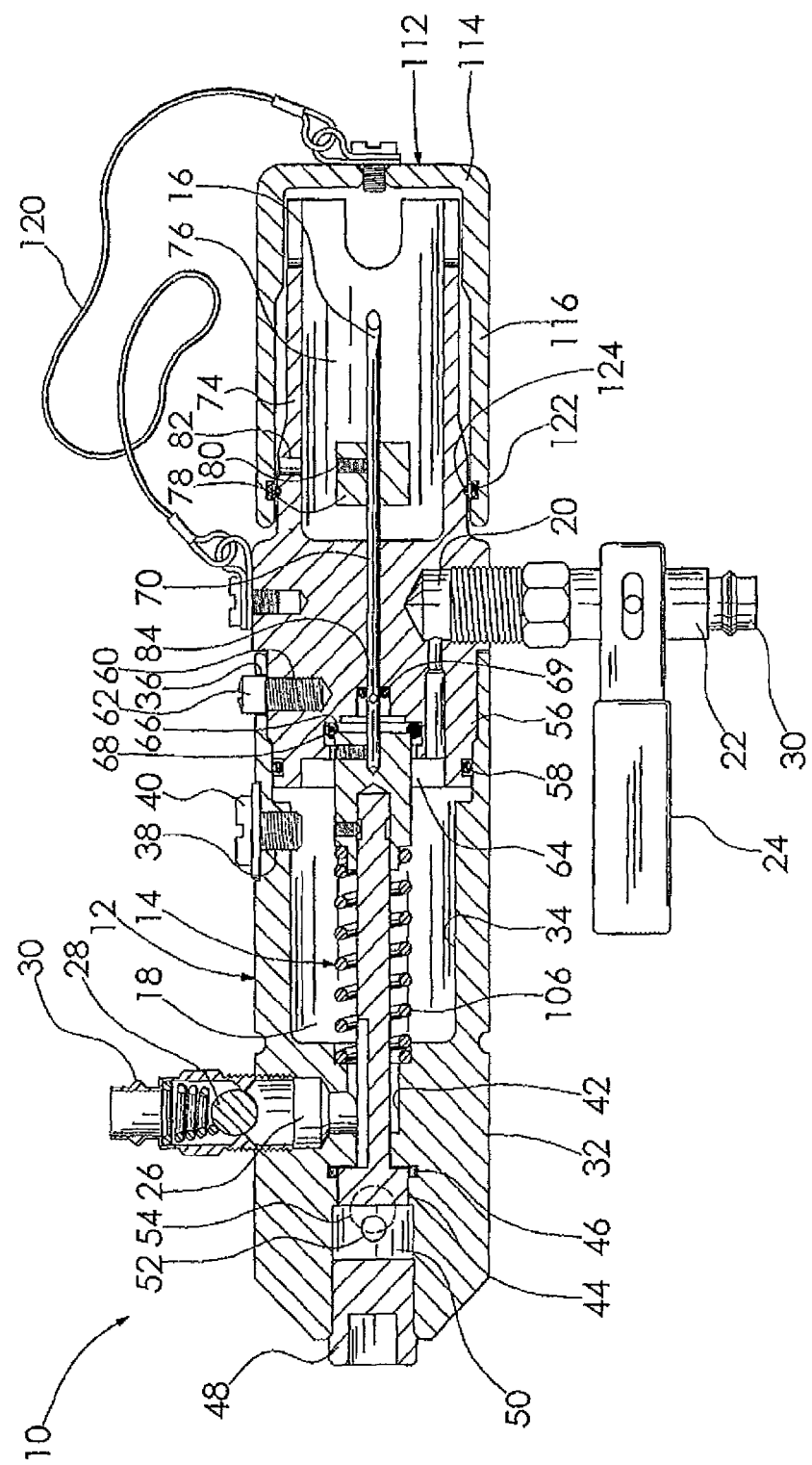
FIG. 1 is an elevational view partly in section of a closed loop system for detecting free water in aviation fuel showing the structural aspects of the invention including a valve assembly slidingly disposed within a collection vessel wherein the valve assembly is maintained in a normally closed position.

The following detailed description and appended drawings describe and illustrate various exemplary embodiments of the invention. The description and drawings serve to enable one skilled in the art to make and use the invention, and are not intended to limit the scope of the invention in any manner. In respect of the methods disclosed, the steps presented are exemplary in nature, and thus, the order of the steps is not necessary or critical.

Referring to the drawings, there is illustrated a closed loop system for collecting a fluid sample from a transient line of fluid, generally indicated by reference numeral 10. The system 10 includes a collection vessel 12 having a valve assembly 14 slideably disposed therein. The collection vessel 12 is adapted to receive a sample of fuel from a source of fuel being tested and includes the valve assembly 14 to create a fluid communication path to facilitate the drawing of the fuel from the collection vessel 12 into a fluid receptacle such as the optically transparent glass fuel test vial 200 clearly illustrated in FIG. 2. In the embodiment shown the fluid communication path is an elongate hollow needle 16. It should be understood that other means for the communication path can be employed to facilitate the transfer of the fuel to other fluid receptacles or testing devices other than the glass vial 200. Further, it should be understood that the system 10 can be used to collect fluid samples from other fluid reservoirs such as a water, an oil, or a chemical reservoir for example.

The collection vessel 12 includes an inlet 20 that provides fluid communication between the source of fuel being tested and a fluid chamber 18 within the collection vessel 12. The collection vessel 12 is also provided with an outlet 26 that provides fluid communication between the fluid chamber 18 and a fuel recovery system (not shown). The fuel recovery system can be any conventional system such as a reservoir, destruction system such as a flare, and the source of fuel, for example.

The inlet 20 includes a valve 22 to control the incoming flow of fuel from the source of fuel. The valve 22 includes an operating spring loaded handle 24 which is biased to a closed position normally preventing the flow of fuel into the closed loop system 10. Initially, an operator opens the valve 22 by moving the handle 24 to an open position. It will be noted that when the operator releases the handle 24, the valve 22 closes automatically.

The outlet 26 includes a check valve 28 to control the discharge of fuel into the recovery system. The check valve 28 facilitates a flow of the fuel through the fluid chamber 18 and into the recovery system when the inlet valve 22 is opened by the operator. Additionally, the check valve 28 retains a sample of fuel in the fluid chamber 18 after the inlet valve 22 is closed, and militates against fuel flowing from the recovery system into the fluid chamber 18.

The closed loop system 10 is typically installed on the piping of an aviation fuel handling system (not shown). The illustrated closed loop system 10 includes a standard quick connect coupler 30 disposed at the inlet 20 and an end of the outlet 26. The disconnect couplers 30 can be used to facilitate the connecting of the closed loop system 10 to the source of fluid and the recovery system, respectively. It should be understood that the closed loop system 10 can be connected to the source of fluid and the recovery system using other connecting devices such as threaded piping, for example.

The collection vessel 12 includes a first member 32 having a cavity 34 formed therein. The cavity 34 is adapted to receive an end of a second member 56. The cavity 34 and the end of the second member 56 form the fluid chamber 18. The first member 32 includes the outlet 26 and the second member 56 includes the inlet 20. It should be understood that the inlet 20 and outlet 26 can be reversed as desired, placing the inlet 20 in the first member 32 and the outlet 26 in the second member 56. Further, other configurations can be used that place both the inlet 20 and the outlet 26 in either the first member 32 or the second member 56.

The second member 56 includes sealing member 58 disposed in an annular groove formed in the outer surface adjacent the end thereof. The sealing member 58 is adapted to facilitate the formation of a substantially fluid tight seal between an inner surface of the cavity 34 and the outer surface of the second member 56. In the illustrated embodiment shown, the sealing member 58 is an O-ring formed of a suitable elastomer that is inert to the fluid sample being obtained. It should be understood that other sealing members can be used as desired. An aperture 36 is formed in the sidewall of the first member 32, and is adapted to align with a threaded bore 60 in the second member 56 to receive a machine screw 62 for securing the first member 32 to the second member 56.

An aperture 38 is formed in the sidewall of the first member 32 to provide access to the fluid chamber 18 and the valve assembly 14 disposed therein. In the embodiment shown, the aperture 38 is adapted to receive a threaded fastener 40 to seal the aperture 38 closed. It should be understood that other means to seal the aperture 38 closed can be used as desired.

A longitudinally extending first conduit 42 is formed in the first member 32 to extend outwardly from the cavity 34 and in fluid communication therewith. The first conduit 42 is adapted to slideably receive one end of the valve assembly 14. The first conduit 42 communicates with the outlet 26 and cooperates with the one end of the valve assembly 14 to form an air vent 44. The air vent 44 provides a communication path between atmospheric air and the fluid chamber 18. The first conduit 42 includes a sealing member 46 adjacent the one end of the valve assembly 14 to form a substantially fluid tight seal between an inner surface of the first conduit 42 and an outer surface of the one end of the valve assembly 14. In the illustrated embodiment shown, the sealing member 46 is an elastomeric O-ring which is received within an annular groove formed in the inner surface of the first conduit 42. The O-ring is formed of a suitable elastomer that is inert to the fluid sample being obtained. It should be understood that other sealing members can be used as desired.

The outer end of the first conduit 42 receives a socket plug 48 that, together with the one end of the valve assembly 14, forms a chamber 50 within the first conduit 42. Another conduit 52 is formed in the sidewall of the first member 32 to provide a communication path for the atmospheric air to enter the chamber 50. Still another conduit 54 is formed in the sidewall of the first member 32 to provide a communication path for atmospheric air to enter the chamber 50. The conduits 52 and 54 cooperate to facilitate the flow of the atmospheric air through the air vent 44 and into the fluid chamber 18 when the air vent 44 is in an open position.

A bore 64 is centrally formed in the end of the second member 56. The bore 64 is adapted to slideably receive an opposite end of the valve assembly 14. A far end of the bore 64 forms a valve seat 66 that cooperates with the opposite end of the valve assembly 14 to selectively close the fluid communication path between the fluid chamber 18 and the associated receptacle. The valve seat 66 includes a sealing member 68 disposed thereon to facilitate the formation of a substantially fluid tight seal between the opposite end of the valve assembly 14 and the valve seat 66. In the illustrated embodiment shown, the sealing member 68 is an O-ring formed of a suitable elastomer that is inert to the fluid sample being obtained. It should be understood that other sealing means can be used as desired.

Figure 2:
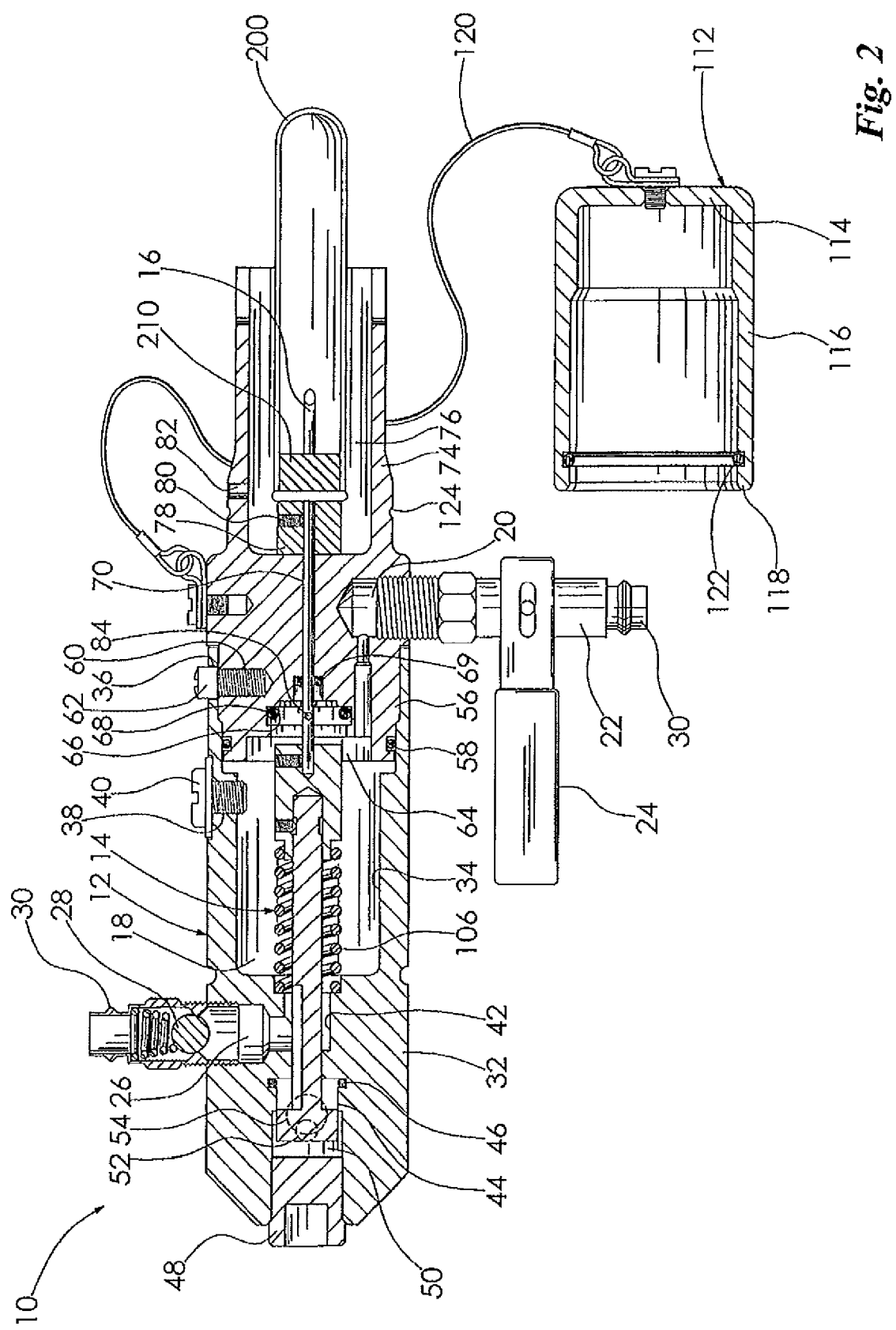
FIG. 2 is an elevational view partly in section of the closed loop system, similar to FIG. 1, showing the structural aspects of the invention with the valve assembly in an open position and having an associated fuel testing vial attached thereto.

As shown in FIG. 2, the communication path between the fluid chamber 18 and the glass vial 200 is the elongate needle 16. A longitudinally extending second conduit 70 is formed in the second member 56. The second conduit 70 is substantially concentric with the bore 64 and is adapted to slidebly receive one end of the needle 16. The one end of the needle 16 extends inwardly from the second conduit 70 and is secured to the end of the valve assembly 14. The spaced apart opposite end of the needle 16 extends outwardly from the second conduit 70 and is accessible for piercing a rubber stopper 210 of the vial 200 as shown in FIG. 2. It should be understood that the opposite end of the needle 16 can be sharpened to facilitate the piercing of the rubber stopper 210. A sealing member 69 is provided in the bore 64 adjacent the second conduit 70 to facilitate the formation of a substantially fluid tight seal between an outer surface of the needle 16 and an inner surface of the second conduit 70. In the illustrated embodiment shown, the sealing means 69 is an O-ring formed of a suitable elastomer that is inert to the fluid sample being obtained. It should be understood that other sealing members can be used as desired.

The needle 16 includes an aperture 84 formed in the sidewall thereof. The aperture 84 is adjacent the opposite end of the valve assembly 14 and provides a fluid communication path from the fluid chamber 18 into the hollow interior of the needle 16.

A skirt 74 extends from the member 56, and defines an internal cavity 76 that encompasses the portion of the needle 16 extending outwardly from the conduit 70. The skirt 74 protects and shields the needle 16 from accidental contact with other objects. Additionally, the cavity 76 is adapted to receive the testing vial 200 as shown in FIG. 2.

A collar 78 is disposed on the needle 16 to restrict the depth of penetration of the needle 16 into the vial 200 and provide a surface for applying a force to cause the valve assembly 14 to slide to an open position. The collar 78 includes a set screw 80 that can be tightened against the needle 16 to secure the collar 78 thereto. A hole 82 adapted to provide access to the set screw 80 is formed in the skirt 74.

Figure 3:
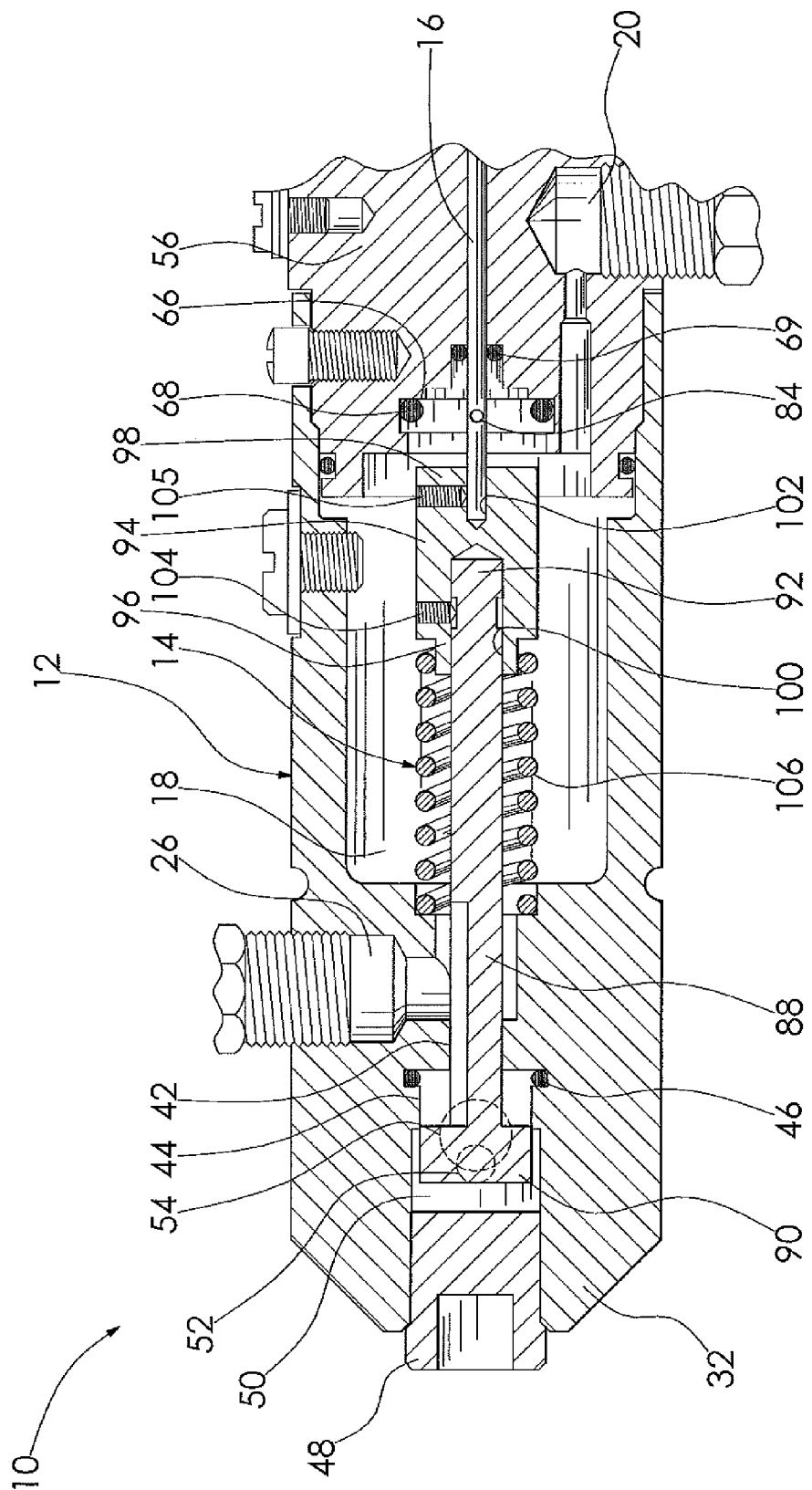
FIG. 3 is an enlarged fragmentary elevational view partly in section of the valve assembly illustrated in FIGS. 1 and 2.

In FIG. 3 the valve assembly 14 is shown slideably disposed within the collection vessel 12 and in the open position. The valve assembly 14 includes an elongate shaft 88, one end 90 of which forms the end of the valve assembly 14 received by the first conduit 42 in the first member 32 and cooperates therewith to form the air vent 44. The other end 92 of the shaft 88 is adapted to attach to one end 96 of a valve body 94. The one end 96 of the valve body 94 includes a bore 100 adapted to receive the end 92 of the shaft 88. A spaced apart end 98 of the valve body 94 is the opposite end of the valve assembly 14 that cooperates with the valve seat 66. The end 98 of the valve body 94 includes a bore 102 adapted to receive the one end of the needle 16. The bore 100 and the bore 102 include attachment means 104 and 105 respectively, to secure the shaft 88 and the needle 16 thereto. In the embodiment shown, the attachment means 104, 105 is a set screw.

The valve assembly 14 includes a helical compression spring 106 which surrounds at least a portion of the shaft 88. The one end of the spring 106 abuts an inner surface of the fluid chamber 18 adjacent the first conduit 42. The other end of the spring 106 abuts the first end 96 of the valve body 94. The spring 106 urges the valve assembly 14 to a closed position.

With renewed reference to FIGS. 1 and 2, a cap 112 is provided for the collection vessel 12. The cap 112 has a closed end 114 with a sidewall 116 depending therefrom. The sidewall 116 terminates in an open end 118 that is adapted to slideably receive the skirt 74 extending from the second member 56 of the collection vessel 12. Sealing means 122 provides a fluid tight seal between the cap 112 and the skirt 74. The sealing means 122 includes an O-ring disposed between an inner surface of the sidewall 116 and a cooperating annular groove 124 formed in the outer surface of the skirt 74. A cord 120 is provided to attach the cap 112 to the collection vessel 12.

In use, once the closed loop system 10 is connected to the source of fuel, the operator opens the inlet valve 22 to permit fuel to enter the closed loop system 10. The incoming fuel flows through the collection vessel 12, past the check valve 28 in the outlet 26, and into the fuel recovery system. The flow of the fuel flushes the air from the fluid chamber 18, as well as flushes any residual fuel that might remain therein from a previous test. Once the flushing process is complete, the inlet valve 22 is closed, stopping the flow of fuel therethrough, and leaving a newly acquired sample of fuel within the fluid chamber 18.

The cap 112 is removed from the skirt 74 of the collection vessel 12. The operator then employs the collection vial 200 to draw the fuel sample from the fluid chamber 18. The collection vial 200 is well known in the fuel testing field. Typically an optically transparent glass vial is used having a rubber stopper 210 at an open end that maintains a vacuum therein. The glass vial 200 holds a powdered chemical (not shown) that is mixed with the fuel sample. The powdered chemical changes color if the fuel contains more than the acceptable amount of free water.

The operator holds the glass vial 200 and places the end with the rubber stopper 210 within the cavity 76 containing the sharpened end of the needle 16. The operator then urges the vial 200 toward the sharpened end of the needle 16, causing the needle 16 to penetrate the rubber stopper 210 and enter the interior space of the vial 200. The operator further urges the vial 200 inwardly until the rubber stopper 210 contacts the collar 78 attached to the needle 16. The operator continues to apply a force to the vial 200 in the same direction, which overcomes the bias of the spring 106. The valve assembly 14 is caused to slide to an open position where the air vent 44 and the fluid communication path between the fluid chamber 18 and the needle 16 are opened. Since the glass vial 200 is under vacuum, the fuel to be tested is drawn from the fluid chamber 18, through the needle 16, and into the vial 200. Air is introduced into the fluid chamber 18 through the open air vent 44 to displace the exiting fuel.

When the vial 200 is filled with fuel, the vial 200 and the associated rubber stopper 210 are removed from the needle 16. At this stage, the spring 106 urges the valve assembly 14 back to the normally closed position causing the closing of the air vent 44 and the communication path between the fluid chamber 18 and the needle 16.

Once removed from the needle 16, the vial 200 is shaken, causing the fuel and the chemical powder previously inserted into the vial 200 to be mixed. The operator visually observes whether the color of the powder has changed to indicate the presence of free water in the fuel.

The operator replaces the cap 112 on the skirt 74 of the collection vessel 12. The O-ring 122 cooperates with the skirt 74 and the cap 112 to create a seal therebetween and militate against contaminants from collecting in the cavity 76 containing the needle 16.

The closed loop system 10 described herein enables an operator to easily obtain a fuel sample from a fueling system. The closed loop system 10 militates against the fuel sample being contaminated prior to testing by isolating the fuel from the external environment as it is directly transferred from the source of fuel, to the collection vessel 12, and into the test vial 200. Further, the closed loop system 10 facilitates obtaining the fuel sample from a source of fuel that supplies the fuel at a pressure greater than atmospheric pressure and stores the fuel within the fluid chamber 18 at a reduced pressure. Unlike the elevated fuel pressure in the source of fluid, the reduced fuel pressure within the fluid chamber 18 militates against damage to the glass vial 200 due to overpressurization.

From the foregoing description, one ordinarily skilled in the art can easily ascertain the essential characteristics of this invention and, without departing from the spirit and scope thereof, can make various changes and modifications to the invention to adapt it to various usages and conditions.

What is claimed is:

1. A closed loop system for collecting a fluid sample from a source of fluid, the closed loop system comprising:

a collection vessel including a fluid chamber disposed therein, wherein the collection vessel includes a first member having a cavity formed in one end, the cavity adapted to receive an end of a second member, the cavity of the first member and the end of the second member forming the fluid chamber;

a valve assembly adapted to selectively open and close a fluid communication path between the fluid chamber and an associated fluid receptacle, wherein the first member includes a first conduit formed therein communicating with the cavity, the first conduit adapted to receive one end of the valve assembly, the first conduit and the one end of the valve assembly forming a vent for the fluid chamber;

an inlet providing fluid communication between the source of fluid and the fluid chamber; and an outlet providing fluid communication between the fluid chamber and a fluid recovery system.

2. The closed loop system according to claim 1, wherein the collection vessel includes a sealing member disposed between an inner surface of the cavity of the first member and an outer surface of the second member adjacent the one end to facilitate the formation of a substantially fluid tight seal therebetween.

3. The closed loop system according to claim 1, wherein the collection vessel includes an aperture formed in a sidewall of the first member and adapted to align with a threaded bore in the second member to receive a threaded fastener to secure the first member to the second member.

4. The closed loop system according to claim 1, wherein the collection vessel includes an aperture formed in a sidewall of the first member that provides access to the fluid chamber, the aperture adapted to receive a threaded fastener to seal the aperture closed.

5. The closed loop system according to claim 1, wherein a sealing member is disposed within the first conduit to form a substantially fluid tight seal between an inner surface forming the conduit and an outer surface of the one end of the valve assembly.

6. The closed loop system according to claim 1, wherein the second member includes a bore at the one end, the bore forming a valve seat and adapted to slideably receive an opposite end of the valve assembly, the valve seat and the opposite end of the valve assembly cooperating to selectively close the fluid communication path between the fluid chamber and the associated fluid receptacle.

7. The closed loop system according to claim 6, wherein a sealing member is disposed on the valve seat to facilitate the formation of a fluid tight seal between the valve seat and the opposite end of the valve assembly.

8. The closed loop system according to claim 6, wherein the valve assembly further comprises:

an elongate shaft having one end and a spaced apart other end, the one end received by the first conduit formed in the first member;

a valve body having one end and a spaced apart other end, the one end including attachment means adapted to secure the other end of the elongate shaft thereto, and the other end of the valve body slideably received by the bore of the second member and contacting the valve seat therein; and a spring having one end and a spaced apart other end, the spring surrounding at least a portion of the elongate shaft, the one end abutting an inner surface of the fluid chamber and the other end abutting the one end of the valve body, the spring urging the valve assembly to a position wherein the vent and the fluid communication path are normally closed.

9. The closed loop system according to claim 8, wherein the fluid communication path includes an elongate hollow needle slideably received in a second conduit formed in the second member, the needle having one end extending through the second conduit and secured to the opposite end of the valve assembly and an opposite end of the needle extending outwardly from the conduit.

10. The closed loop system according to claim 9, wherein the needle includes an aperture formed in a wall thereof adjacent the opposite end of the valve assembly, the needle and the aperture therein providing the fluid communication path from the fluid chamber to the associated fluid receptacle when the valve assembly is in an open position.

11. The closed loop system according to claim 10, wherein a sealing member is disposed in the bore adjacent the second conduit to form a substantially fluid tight seal between an inner surface forming the second conduit and an outer surface of the needle.

12. The closed loop system according to claim 11, wherein the needle includes a collar disposed thereon.

13. The closed loop system according to claim 9, wherein a skirt extends from the second member, the skirt defining an internal cavity that receives the opposite end of the needle therein.

14. The closed loop system according to claim 13, wherein a cap is provided that is slidebly received over the skirt.

15. The closed loop system according to claim 1, wherein the inlet includes a normally closed valve.

16. A closed loop system for collecting a fluid sample from a source of fluid, the closed loop system comprising:

a collection vessel including a fluid chamber disposed therein;

a valve assembly adapted to selectively open and close a fluid communication path between the fluid chamber and an associated fluid receptacle;

an inlet providing fluid communication between the source of fluid and the fluid chamber; and an outlet providing fluid communication between the fluid chamber and a fluid recovery system, wherein the outlet includes a check valve.

17. A closed loop system for collecting a fluid sample from a source of fluid, the closed loop system comprising:

a collection vessel including a fluid chamber disposed therein;

a valve assembly adapted to selectively open and close a fluid communication path between the fluid chamber and an associated fluid receptacle, the valve assembly including:

an elongate shaft having one end and a spaced apart other end;

a valve body having one end and a spaced apart other end, the one end including attachment means adapted to secure the other end of the elongate shaft thereto; and a spring having one end and a spaced apart other end, the spring surrounding at least a portion of the elongate shaft, the one end abutting an inner surface of the fluid chamber and the other end abutting the one end of the valve body, the spring urging the valve assembly to a position wherein the fluid communication path is normally closed;

an inlet providing fluid communication between the source of fluid and the fluid chamber; and an outlet providing fluid communication between the fluid chamber and a fluid recovery system.

18. A method for collecting a fluid sample from a transient line of fluid comprising the steps of:
providing a collection vessel in fluid communication with the transient line of fluid;
opening a valve to cause the fluid to flow from the transient line through the collection vessel;
retaining a sample of the fluid in a fluid chamber within the collection vessel; and
drawing the sample of fluid from the fluid chamber through a communication path into a fluid receptacle.

19. The method of claim 18, wherein:
the collection vessel comprises a first member having a cavity formed in one end, the cavity adapted to receive an end of a second member, the cavity of the first member and the end of the second member forming the fluid chamber; and
the communication path includes a valve assembly adapted to selectively open and close the communication path, wherein the first member includes a first conduit formed therein communicating with the cavity, the first conduit adapted to receive one end of the valve assembly, the first conduit and the one end of the valve assembly forming a vent for the fluid chamber;
further comprising venting the fluid chamber while drawing the sample of fluid from the fluid chamber through the communication path into the fluid receptacle.

20. The method of claim 18, wherein the transient line of fluid is at a pressure greater than atmospheric pressure and the sample of the fluid retained in the fluid chamber within the collection vessel is at a reduced pressure compared to the transient line of fluid.

* * * * *